United States Patent [19]

Ohlendorf et al.

[11] Patent Number: 4,924,004
[45] Date of Patent: May 8, 1990

[54] 1-PHENYL-2-AMINOCARBONYLINDOLE COMPOUNDS, PREPARATION THEREOF AND PHARMACEUTICAL COMPOSITIONS CONTAINING THEM

[75] Inventors: Heinrich-Wilhelm Ohlendorf; Wilhelm Kaupmann, both of Hanover; Ulrich Kuehl, Gehrden; Gerd Buschmann; Stephen Magda, both of Hanover, all of Fed. Rep. of Germany

[73] Assignee: Kali-Chemie Pharma GmbH, Hanover, Fed. Rep. of Germany

[21] Appl. No.: 264,049

[22] Filed: Oct. 28, 1988

Related U.S. Application Data

[60] Division of Ser. No. 885,684, Jul. 15, 1986, Pat. No. 4,803,198, which is a continuation of Ser. No. 648,932, Sep. 10, 1984, abandoned, which is a continuation of Ser. No. 402,766, Jul. 28, 1982, abandoned.

[30] Foreign Application Priority Data

Aug. 8, 1981 [DE] Fed. Rep. of Germany ....... 3131527

[51] Int. Cl.$^5$ ................. C07D 491/056; C07D 209/42
[52] U.S. Cl. .................................... 548/431; 548/454; 548/484
[58] Field of Search ........................ 548/431, 454, 484

[56] References Cited

FOREIGN PATENT DOCUMENTS 869014 10/1962 France .

OTHER PUBLICATIONS

M. Mottet, Chem. Abstracts, vol. 69:106400v (1968).
A. Prudchenko et al., Chem. Abstracts, vol. 73:14788g (1970).

*Primary Examiner*—Mary E. Ceperley
*Attorney, Agent, or Firm*—Foley & Lardner, Schwartz, Jeffery, Schwaab, Mack, Blumenthal & Evans

[57] ABSTRACT

New 1-phenyl-2-aminocarbonylindole compounds are described which have the general formula I

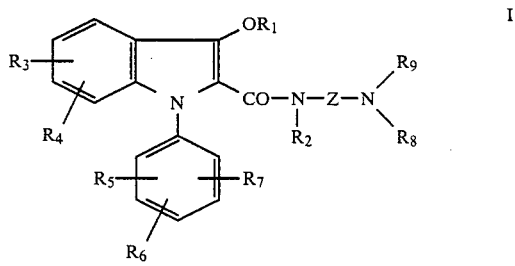

where $R_1$ is a hydrogen atom, or a lower alkyl, alkenyl, cycloalkyl or cycloalkylalkyl radical, $R_2$ is a hydrogen atom or a lower alkyl radical, $R_3$ is a hydrogen or halogen atom, or a lower alkyl, hydroxyl or lower alkoxy radical, $R_4$ is a hydrogen or halogen atom, or a lower alkyl, hydroxyl or lower alkoxy radical, or, if $R_3$ is a hydrogen atom, $R_4$ may be a nitro or trifluoromethyl radical, or $R_3$ and $R_4$ together denote a methylenedioxy or ethylenedioxy radical, $R_5$ has the meanings given for $R_3$, $R_6$ has the meanings given for $R_4$, $R_7$ is a hydrogen atom or, if $R_5$ and $R_6$ are lower alkoxy radicals, $R_7$ may also be a lower alkoxy radical, $R_8$ and $R_9$ are each a hydrogen atom or a lower alkyl radical or, together with the nitrogen atom, form a heterocyclic group, and Z is a alkylene chain which is optionally substituted by hydroxyl. The compounds have pharmacological properties, in particular antiarrhythmic properties. The compounds may be in the form of the free base or acid addition salts. Pharmaceutical compositions containing these compounds are described as is a method of preparing them.

Valuable intermediates for the production of these compounds and methods of preparing the intermediates are also described.

2 Claims, No Drawings

1-PHENYL-2-AMINOCARBONYLINDOLE COMPOUNDS, PREPARATION THEREOF AND PHARMACEUTICAL COMPOSITIONS CONTAINING THEM

This application is a division of application Ser. No. 885,684, now U.S. Pat. No. 4,803,198 filed July 15, 1986, which is a continuation of Ser. No. 648,932, now abandoned filed September 10, 1984, which in turn is a continuation of Ser. No. 402,766 filed July 28, 1982, now abandoned.

BACKGROUND OF THE INVENTION

The present invention relates to new 1-phenyl-2-aminoalkylaminocarbonylindole compounds and salts thereof, to pharmaceutical compositions containing these compounds, to a method for the manufacture of these compound and to intermediate products for use in the manufacture of these compounds.

U.S. Pat. No. 3,573,325 describes 2-carboamidoindole compounds which have antiemetic properties and a depressant action on the central nervous system, and U.S. Pat. No. 3,198,807 describes 2-carboxamidoindole compounds which also have antiemetic properties and, in addition, local anaesthetic and antifibrillatory properties.

SUMMARY OF THE INVENTION

It is an object of the invention to develop new 1-phenyl-2-aminocarbonylindole compounds with valuable pharmacological properties.

It has been found that the new 1-phenyl-2-aminocarbonylindole compounds of this invention have valuable pharmacological properties, in particular antiarrhythmic properties, and display an advantageous action profile with a good therapeutic range and low toxicity. On the basis of these actions, the new compounds are suitable as pharmaceuticals, in particular for the treatment of disorders in cardiac rhythm.

According to one aspect of the present invention there is provided a 1-phenyl-2-aminocarbonylindole compound of the general formula I

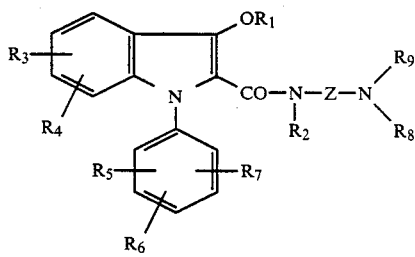

wherein $R_1$ is a hydrogen atom or an alkyl, alkenyl, cycloalkyl or cycloalkylalkyl radical with up to 7 carbon atoms, $R_2$ is a hydrogen atom or a lower alkyl radical, $R_3$ is a hydrogen or halogen atom, or a lower alkyl, hydroxyl or lower alkoxy radical, $R_4$ is a hydrogen or halogen atom or a lower alkyl, lower alkoxy or hydroxyl radical, or, if $R_3$ is a hydrogen atom, $R_4$ may be a nitro or trifluoromethyl radical, or $R_3$ and $R_4$ are bonded to adjacent carbon atoms and together denote a methylenedioxy or ethylenedioxy radical, $R_5$ is a hydrogen or halogen atom, or a lower alkyl, hydroxyl or lower alkoxy radical, $R_6$ is a hydrogen or halogen atom, or a lower alkyl, lower alkoxy or hydroxyl radical, or, if $R_5$ is a hydrogen atom, $R_6$ may be a nitro or trifluoromethyl radical, or $R_5$ and $R_6$ are bonded to adjacent carbon atoms and together denote a methylenedioxy or ethylenedioxy radical, $R_7$ is a hydrogen atom or, if $R_5$ and $R_6$ are lower alkoxy radicals, $R_7$ may also be a lower alkoxy radical, $R_8$ is a hydrogen atom or lower alkyl radical and $R_9$ is a hydrogen atom or lower alkyl radical, or $R_8$ and $R_9$, together with the nitrogen atom to which they are bonded, form a heterocyclic group a

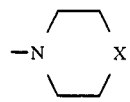

where X represents a bond, an oxygen or sulphur atom, or a —CH$_2$— or —C$_2$H$_4$— radical, and Z is an alkylene chain has 2–5 carbon atoms and which is optionally substituted by hydroxyl on a carbon atom which is not bonded to nitrogen; and acid addition salts of the compound of formula I.

If the substituents $R_3$ to $R_7$ of the carbocyclic aromatic rings in the compounds of the formula I contain a lower alkyl group, this can be straight-chain or branched and can contain 1-4 carbon atoms. Suitable alkyl radicals include methyl, ethyl, n-propyl, isopropyl, n-butyl and tert.-butyl, preferably methyl and ethyl. Especially in the case of where the rings are disubstituted or trisubstituted, the alkyl and alkoxy substituents are preferably methyl and methoxy radicals.

Possible halogen substituents in the carbocyclic aromatic rings include fluorine, chlorine and bromine, chlorine and bromine being preferred.

The substituents $R_3$ and $R_4$ are preferably hydrogen or halogen atoms and the substituents $R_5$, $R_6$ and $R_7$ are preferably hydrogen or halogen atoms or lower alkyl radicals.

The substituent $R_1$ is a hydrogen atom or a straight-chain branched or cyclic alkyl or alkenyl radical with up to 7 carbon atoms. In particular, $R_1$ is a hydrogen atom or a lower alkyl radical, preferably a methyl, or cycloalkylalkyl radical. Possible lower alkyl radicals are straight-chain or branched $C_1$–$C_4$ alkyl groups. Examples of suitable lower alkyl and cycloalkylalkyl groups include methyl, ethyl, n-propyl, isopropyl, tert.-butyl and cyclopropylmethyl radicals.

The substituent $R_2$ is preferably a hydrogen atom, but if $R_2$ is a lower alkyl radical, this is preferably a methyl or ethyl radical.

If $R_8$ and/or $R_9$ is a lower alkyl this may be a straight chain or branched $C_1$–$C_4$-alkyl and is preferably a methyl, ethyl, propyl or butyl radical. In particular, the

may be a dialkylamino radical containing unbranched alkyl radicals, and may be, for example, the diethylamino radical.

Z is an alkylene chain with 2 to 5 carbon atoms, preferably a straight alkylene chain with 2 to 4 carbon atoms. If Z is an alkylene chain substituted by hydroxyl, this is preferably the 2-hydroxypropylene chain.

According to another aspect of the present invention, there is provided a method for the preparation of a 1-phenyl-2-aminocarbonylindole compound of the general formula I

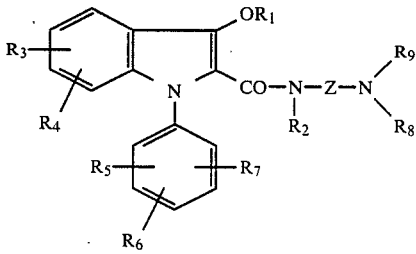

where $R_1$, $R_2$, $R_3$, $R_4$, $R_5$, $R_6$, $R_7$, $R_8$, $R_9$ and Z have the meanings defined above, wherein a compound of the general formula

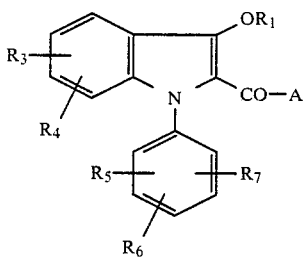

is reacted with a compound of the formula

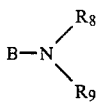

where A and B are reactive to produce an

linkage between said two compounds,
and where
A is a hydroxyl radical or reactive group, when B is

A is

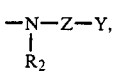

when B is a hydrogen atom
A is

when B is a Hal-Z-, or
A is

when B is U', where $R_1$, $R_2$, $R_3$, $R_4$, $R_5$, $R_6$, $R_7$, $R_8$, $R_9$ and Z have the meanings defined above, Y is a reactive group, Hal is a halogen atom, and one of U and U' is a hydrogen atom and the other is a

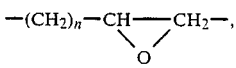

and n is 1, 2 or 3, and wherein, if desired, a free compound of formula I is converted into its acid addition salt or the acid addition salt is converted into the free base.

DETAILED DESCRIPTION OF THE INVENTION AND ITS EMBODIMENTS

In one particular embodiment of this method a new 1-phenyl-2-aminocarbonylindole compound of formula I and acid addition salts thereof may be obtained by reacting a compound of formula II

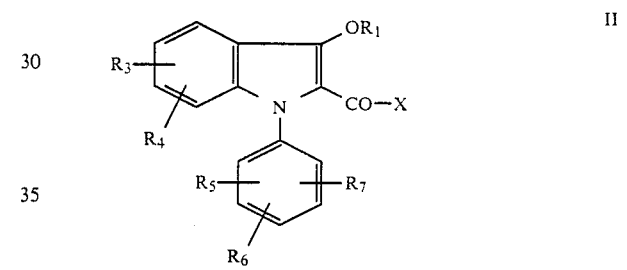

wherein $R_1$, $R_3$, $R_4$, $R_5$, $R_6$ and $R_7$ have the above defined meanings and X is hydroxyl or a reactive group, with a compound of the formula VI

where $R_2$, $R_8$, $R_9$ and Z have the above defined meanings.

In another embodiment of this method, a compound of the formula III

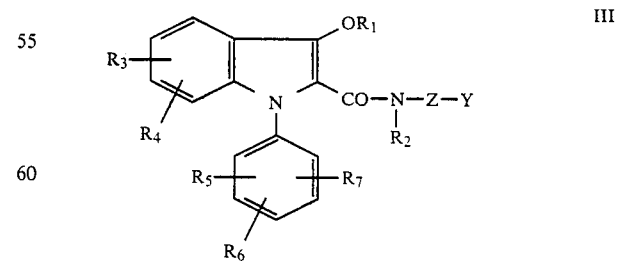

where $R_1$, $R_2$, $R_3$, $R_4$, $R_5$, $R_6$, $R_7$ and Z have the above defined meanings and Y is a group which can be split off by aminolysis, is reacted with a compound of the formula VII

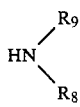

where $R_8$ and $R_9$ have the above defined meanings.

In a further embodiment of this method, a compound of the formula IVa

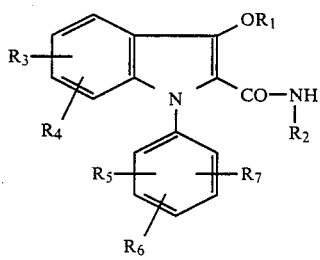

where $R_1$, $R_2$, $R_3$, $R_4$, $R_5$, $R_6$ and $R_7$ have the above defined meanings, is reacted with a compound of the formula VIII

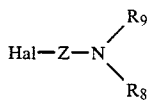

where Z, $R_8$ and $R_9$ have the above defined meanings and Hal is a halogen atom.

In yet another embodiment of the method for the preparation of a compound of the formula Ia

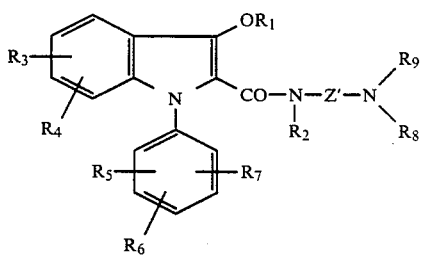

where $R_1$, $R_2$, $R_3$, $R_4$, $R_5$, $R_6$, $R_7$, $R_8$ and $R_9$ have the above defined meanings and Z' is an alkylene group which has 2–5 carbon atoms and is substituted by hydroxyl on a carbon atom which is not bonded to nitrogen, a compound of the formula IV

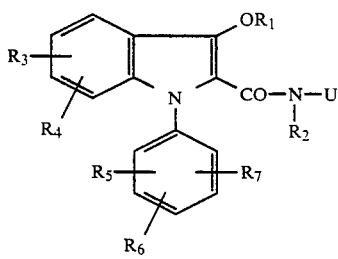

where $R_1$, $R_2$, $R_3$, $R_4$, $R_5$, $R_6$ and $R_7$ have the above defined meanings and U is a hydrogen atom or a radical of the formula V

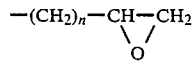

where n is 1, 2 or 3, is reacted with a compound of the formula IX

where $R_8$ and $R_9$ have the above defined meanings and, if U is a hydrogen atom, U' is a radical of formula V, or, if U is a radical of formula V, U' is a hydrogen atom.

In each of these embodiments, if the compound of formula I is obtained in the form of the free compound it may be converted into the acid addition salt or, if it is obtained in the form of the acid addition salt, it may be converted into the free compound of formula I.

The reaction of the acid or acid derivative of formula II with the amine of the formula VI can be carried out by methods which are customary per se for the formation of amide groupings by aminoacylation, using an acid of the formula II (X=OH) or a reactive derivative thereof wherein X denotes a reactive group. Possible reactive derivatives include, acid halides, preferably chlorides, esters and mixed anhydrides of the acids of the formula II, for example compounds of the formula II wherein the reactive group X denotes halogen, in particular chlorine or bromine, lower alkoxy, in particular alkoxy with 1 to 4 carbon atoms, or an O-CO-W group, wherein W is a lower alkyl or lower alkoxy radical. The acylation can be carried out in a solvent which is inert under the reaction conditions, at a temperature between room temperature and the boiling point of the solvent. Suitable solvents include halogenated hydrocarbons, such as methylene chloride or chloroform, aromatic hydrocarbons, such as benzene, toluene, xylene or chlorobenzene, cyclic ethers, such as tetrahydrofuran or dioxane, dimethylformamide and mixtures of these solvents.

If appropriate, especially if an acid halide or anhydride of formula II is used, the acylation can be carried out in the presence of an acid-binding reagent. Suitable acid-binding agents include inorganic bases, in particular alkali metal carbonates and hydroxides, such as, for example, sodium carbonate potassium carbonate or potassium hydroxide, and organic bases, in particular tertiary lower alkylamines and pyridines, such as, for example, triethylamine, tripropylamine, tributylamine, pyridine, 4-dimethylaminopyridine and 4-pyrrolidinopyridine. Instead of an additional base, it is also possible to use an excess of the amine of formula VI. Organic bases used in excess can simultaneously also serve as the solvent.

If an acid of the formula II itself or an ester thereof is used, the reaction of the acid or of the ester with the amine of the formula VI is advantageously carried out in the presence of a coupling reagent known from peptide chemistry to be suitable for amide formation. Examples which may be mentioned of coupling reagents which promote the amide formation fo the free acids by reacting with the acid in situ to form a reactive acid derivative are alkylcarbodiimides, preferably cycloalkylcarbodiimides, especially dicyclohexylcarbodiimide, carbonyldiimidazole and N-lower alkyl-2- halopyridinium salts, in particular halides or tosylates, preferably N-methyl-2-chloropyridinium iodide (see, for example, Mukayama in Angew, Chemie 91 789–812). The reaction in the presence of a coupling reagent can advantageously be carried out a a temperature from −30° C. to +30° C., using a solvent such as a halogenated hydrocarbon and/or aromatic solvent, if desired, in the presence of an acid-binding amine. Examples which may be mentioned of coupling reagents which promote amide formation of the esters by formation of a reactive derivative of the amino compound include tri-lower alkyl-aluminium compounds, in particular trimethylaluminium, which is suitable for activating the reaction of the amino compounds with esters, or phosphorus trichloride. Suitable inert solvents for the reaction in the presence of trialkylaluminium include, in particular, aromatic hydrocarbons and/or halogenated hydrocarbons. The reaction of the amino compound with the trialkylaluminium is preferably carried out at a temperature from −20° C. to room temperature. Subsequent reaction of the intermediately formed monoalkylaluminiumazo compound with the ester can be carried out, in particular, at a temperature between room temperature and the boiling point of the solvent. Further coupling reagents which are suitable for amide formation and are also used in peptide syntheses are known, for example, from Advanced Organic Chemistry by Jerry March, McGraw-Hill Ltd., 2nd Edition, pages 382–388 and The Chemistry of Amides, by Jacob Zabicky 1970, Interscience Publishers, John Wiley & Sons, London, Chapter 2: Synthesis of Amides.

If the starting compounds contain free hydroxyl groups, prior to the reaction, these can, if desired, be provided with a protective group, which can subsequently easily be split off again, in a manner which is known per se. Suitable protective groups which can easily be split off again after the reaction are known, for example, from E. McOmie "Protective Groups in Organic Chemistry" Plenum Press 1971. Esters, for example, acetates, and ethers which can easily be split, in particular tetrahydropyranyl ethers, are suitable, for example, for protection of a hydroxyl group.

The reaction of a compound of formula III with an amine fo formula VII can be carried out by methods which are customary per se for aminoalkylation. The reaction is advantageously carried out at an elevated temperature, for example at a temperature of from 50° C. to 150° C., under basic conditions. Preferred substituents Y which can be split off by aminolysis in compounds of formula III include halogen atoms, such as chlorine, bromine and iodine, and organic sulphonic acid radicals, in particular radicals of lower alkanesulphonic acids, such as, for example, methanesulphonic acid or ethanesulphonic acid, or of aromatic sulphonic acids, in particular benzene-sulphonic acid or benzenesulphonic acids which are substituted by lower alkyl, for example toluenesulphonic acids, or benzenesulphonic acids which are substituted by halogen, such as, for example, bromobenzenesulphonic acids. The reaction is advantageously carried out in an organic solvent which is inert under the reaction conditions. Examples of suitable solvents which may be mentioned are aromatic hydrocarbons, such as benzene, toluene and xylene, cyclic ethers, such as dioxane, dimethylformamide, 1,3-dimethyl-2-imidazolidinone, hexamethylphosphoric acid triamide, sulpholane, dimethylsulphoxide, tetramethylurea and alkyl alcohols, for example isopentanol. If desired, the reaction of the compounds of formula III with the amine of the formula VII can, however, also be carried out in the melt, without a solvent. The reaction can advantageously be carried out with the addition of an organic or inorganic base. However, it is also possible to use an excess of the compound of formula VII and to use this as an internal base. Suitable inorganic bases include, alkali metal carbonates or bicarbonates, such as sodium carbonate, sodium bicarbonate or potassium carbonate. Suitable organic bases include tertiary organic amines, in particular tertiary lower alkylamines, such as triethylamine, n-tripropylamine, n-tributylamine and 1,4-dimethylpiperazine.

The reaction of an amide of formula IVa with an alkyl halide compound of formula VIII can be carried out in a manner which is known per se. The reaction is advantageously carried out in a solvent which is inert under the reaction conditions, with the addition of an organic or inorganic base, for example one of the above-mentioned bases, at an elevated temperature, for example at a temperature of from 50° C. to 120° C., preferably at the boiling point of the solvent. Examples of suitable inert solvents include cyclic ethers, such as dioxane or tetrahydrofuran, dimethylformamide and lower alkyl ketones, such as acetone.

The reaction of a compound of formula IV with a compound of formula IX can be carried out in the manner which is customary per se for the reaction of epoxides. The reaction is advantageously carried out in a solvent which is inert under the reaction conditions, at a temperature of from room temperature to 100° C. Examples of suitable solvents include aromatic hydrocarbons, such as benzene, toluene and xylene, open or cyclic ethers, such as, for example, diethyl ether, tetrahydrofuran and dioxane, and lower alcohols, such as for example, isopropanol.

If the compound of formula III, IVa or IV contains one or more free hydroxyl groups, these are advantageously provided with a protective group during the above reactions in a manner which is known per se.

Compounds of formula I where Z contains a hydroxyl group are obtained, in the synthesis, in the form of their racemates. The present invention is concerned with the racemic mixtures as well as the optically active forms of these compounds. The racemic mixtures can be resolved into their optically active antipodes in a manner which is known per se by reaction with suitable optically active acids, such as, for example, tartaric acid, O,O'-dibenzoyl-tartaric acid, mandelic acid or di-O-isopropylidene-2-oxo-L-gulonic acid, and subsequent fractional crystallisation of the salts obtained.

The compounds of formula I can be isolated from the reaction mixture, and purified, in a manner which is known per se. Acid addition salts can be converted into the free bases in the customary manner, and, if desired, these can be converted into pharmacologically acceptable acid addition salts in a known manner.

Examples of suitable pharmacologically acceptable acid addition salts of the compounds of the formula I are their salts with hydrochloric acid, hydrobromic acid, sulphuric acid, phosphoric acid, methanesulphonic acid, ethanesulphonic acid, cyclohexylaminosulphonic acid, amidosulphonic acid, acetic acid, lactic acid, tartaric acid, phenylacetic acid or mandelic acid.

Compounds of formula II are valuable intermediate products for the preparation of pharmacologically active compounds, for example the compounds of the formula I.

Compounds of the following formula IIa

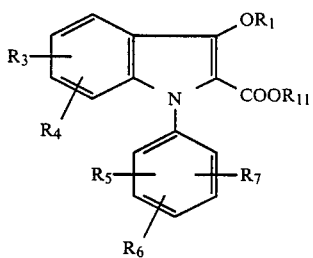

IIa where $R_1$, $R_3$, $R_4$, $R_5$, $R_6$ and $R_7$ have the above defined meanings and $R_{11}$ is a lower alkyl radical, can be obtained in a manner which is known per se, by a process in which (a') a compound of the formula X

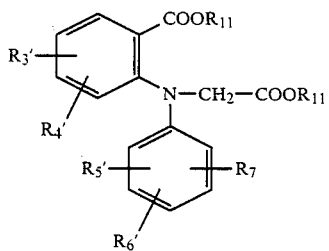

X where $R_7$ and $R_{11}$ have the above defined meanings and $R_3'$, $R_4'$, $R_5'$ and $R_6'$ in each case have the meanings given for $R_3$, $R_4$, $R_5$ and $R_6$, but any free hydroxyl group is provided with a protective group is cyclised in a manner which is known per se to give a compound of formula IIb

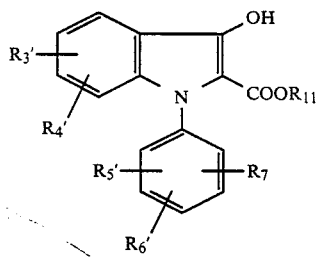

IIb where $R_3'$, $R_4'$, $R_5'$, $R_6'$, $R_7$ and $R_{11}$ have the above defined meanings, and, if desired, this compound is etherified to give a compound of formula IIc

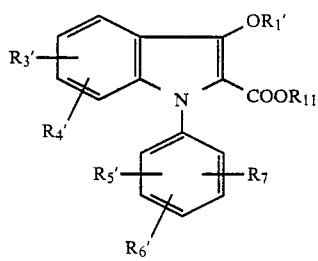

IIc where $R_3'$, $R_4'$, $R_5'$, $R_6'$, $R_7$ and $R_{11}$ have the above defined meanings and $R_1'$ has the meaning given for $R_1$, with the exception of hydrogen, and any hydroxyl-protective groups present are split off again in a manner which is known per se, or (b') a compound of the formula XI

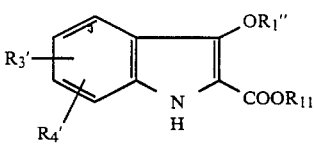

XI where $R_3'$, $R_4'$ and $R_{11}$ have the above defined meanings as $R_1''$ has the meaning given for $R_1'$ or is a lower acyl protective group, is reacted with a compound of the formula XII

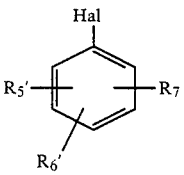

XII where $R_5'$, $R_6'$, $R_7$ and Hal have the above defined meanings, and any acyl protective group $R_1''$ present and/or any hydroxyl-protective group present is split off in a manner which is known per se.

The compounds of formula IIa can then be hydrolysed to the corresponding acids in a manner which is known per se, and these can be converted into further reactive acid derivatives in a manner which is also known per se. Hydrolysis of esters of the formula IIa to the corresponding acids can be carried out in an alkaline or acid medium by methods which are customary for ester hydrolysis, for example by heating the ester in an aqueous alkali metal hydroxide solution, advantageously in a presence of a water-miscible inert organic solvent, for example a lower alcohol. The free acids of formula II are likewise converted into reactive acid derivatives in a manner which is known per se. Thus, an acid halide of formula II can be otained, for example, by reacting the acid with an inorganic acid halide, for example phosphorus trichloride, phosphorus pentachloride, phosphorus tribromide or thionyl chloride. If desired, the reaction can be carried out in the presence of pyridine or another tertiary organic base. Mixed acid anhydrides can be obtained, for example by reacting an alkali metal salt of the acid of the formula II with a corresponding organic acid chloride in the presence of tertiary organic base, for example pyridine.

The cyclisation of the compounds of formula X according to process variant (a') is advantageously carried out in a solvent which is inert under the reaction conditions, in the presence of a strong base at elevated temperature, for example at a temperature of from 50° C. to 150° C. Examples of suitable strong bases include alkali metal hydrides, such as sodium hydride, and alkali metal lower alcoholates, such as, for example, sodium methylate. Examples of suitable inert solvents include aromatic hydrocarbons, such as toluene and xylene, lower alcohols, dimethylformamide and mixtures of such solvents. Thus, for example, aromatic hydrocarbons or dimethylformamide are particularly suitable solvents if alkali metal hydrides are used, and if alkali metal alcoholates are used, the corresponding alcohols are particularly suitable solvents. In the reaction, the compound of formula IIb is obtained in the form of its alkali metal salt and can be liberated, during working up, by acidification of the reaction mixture.

Etherification of compounds of formula IIb to give compounds of formula IIc can be carried out by methods which are known per se, for example by reacting a compound of formula IIb with a compound of formula XIII $$R_1'\text{-}X_1 \qquad \text{XIII}$$

where $R_1'$ has the above defined meaning and $X_1$ is a halogen atom, preferably a chlorine atom, or, if $R_1'$ is a methyl or ethyl radical, the corresponding $R_1'\text{-}SO_4$ radical, in the presence of a base and in the presence of an inert solvent. If a halide, in particular a chloride, of the formula XIII is used as the alkylating agent, it is advantageous to use an alkali metal salt of the compound of formula IIb, or a base which is so strong that it is capable of forming an alkali metal salt with the compound of the formula IIb in situ. Examples of suitable bases of this type are alkali metal hydrides and alkali metal alcoholates. If a dialkyl sulphate is used as the alkylating agent, any desired inorganic base, for example an alkali metal carbonate or hydroxide, such as, for example, potassium carbonate or potassium hydroxide, can be used. Suitable inert solvents include aromatic hydrocarbons, lower alcohols, dimethylformamide and, if inorganic bases are used, lower ketones, such as acetone. If desired, the alkali metal salts of the compound of formula IIb which are formed during the cyclisation can also be used directly in the etherification, without prior isolation of the compound of the formula IIb.

Suitable hydroxyl-protective groups are groups which can be split off by hyrodlysis or hydrogenolysis, for example benzyl or lower acyl groups.

The starting compounds of formula X required for process variant (a') can be obtained in a manner which is known per se, starting from phenylglycine compounds of formula XIV

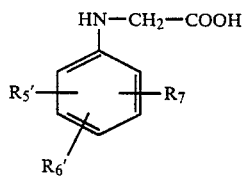

where $R_5'$, $R_6'$ and $R_7$ have the above defined meanings, and which can be obtained by reacting the corresponding aniline with chloroacetic acid, and a o-chlorobenzoic acid of formula XV

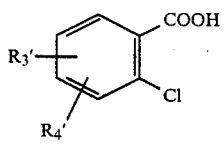

where $R_3'$ and $R_4'$ have the above defined meanings. The alkali metal salt, in particular the potassium salt, of the acid of formula XIV is reacted with the alkali metal salt, in particular the potassium salt, of the acid of formula XV at elevated temperature, for example a temperature of from 100° to 150° C., in the presence of an inorganic base, for example potassium carbonate, and of a copper catalyst, for example copper powder, in a polar solvent, preferably water or a mixture of water and a water-miscible organic solvent, to give a compound of the formula XVI

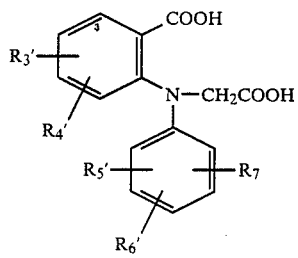

where $R_3'$, $R_4'$, $R_5'$, $R_6'$ and $R_7$ have the above defined meanings, and the compound is then esterified in a manner which is known per se to give a compound of formula X, for example by reaction with an alcohol $R_{11}OH$ in the presence of sulphuric acid at elevated temperature, for example at the boiling point of the reaction mixture.

Process variant (a') described above is particularly suitable for the preparation of those compounds of formula IIa where $R_3$ and $R_4$ are hydrogen or are substituents which are not capable of reacting with phenylglycine. If the compound of formula XV contains other substituents which are capable of reacting with phenylglycine, polysubstituted by-products, in addition to the compound of the formula XVI, can also be formed in the reaction mixture in this reaction. The desired reaction product can be separated off from any by-products present by a chromatographic route.

The reaction of a compound of formula XI with a compound of formula XII according to process variant (b') can be carried out in a manner which is known per se. The compound of formula XI is advantageously reacted in the form of its alkali metal salt, for example the sodium or lithium salt, with a compound of formula XII in a solvent which is inert under the reaction conditions, at temperatures of from about 100° to 170° C. Suitable solvents include inert organic solvents with boiling points within the temperature range given, preferably dimethylformamide. It is advantageous to carry out the reaction in the presence of a copper catalyst, for example copper powder or a copper-I or copper-II halide. If desired, the alkali metal salt of the compound of formula XI can be prepared in situ by reaction with a strong base, for example an alkali metal alcoholate, hydride or hydroxide. Suitable lower acyl protective groups for the preparation of 3-hydroxyindole compounds of formula IIa are acyl radicals with 2 to 5 carbon atoms, preferably the acetyl radicals.

The starting compounds of formula XI required for process variant (b') can be prepared in a manner which is known per se, starting from an anthranilic acid ester of the formula XVII

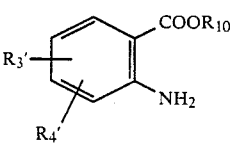

where $R_2$, $R_3$ and $R_4$ have the above defined meanings and $R_{10}$ is a lower alkyl radical, by a process in which the compound is first reacted with chloroacetic acid or a chloroacetic acid lower alkyl ester in a manner which is known per se to give a compound of the formula XVIII

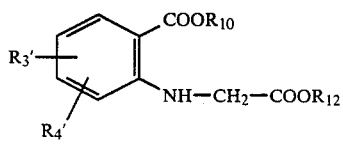

where $R_3'$, $R_4'$ and $R_{10}$ have the above defined meanings and $R_{12}$ is a hydrogen atom or a lower alkyl radical, and, if $R_{12}$ is a hydrogen atom, esterifying the acid with an alcohol $R_{11}OH$, where $R_{11}$ has the above defined meaning, in a manner which is known per se, and cyclising the resulting diester in a manner which is also known per se to give a compound of the formula XIX

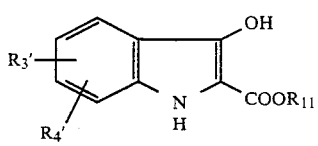

where $R_3'$, $R_4'$ and $R_{11}$ have the above defined meanings, which is then converted into a compound of formula XI in a manner which is known per se, by etherification or esterification of the hydroxyl group. The cyclisation of the ester of formula XVIII can be carried out, for example, under the conditions described above for cyclisation of the ester of formula X. The etherification of the compound of formula XIX can be carried out, for example, under the conditions described above for the etherification of the compound of formula IIb.

Process variant (b') is particularly suitable for the preparation of those compounds of the formula IIa where $R_5$ to $R_7$ are hydrogen atoms or those substituents which are not capable of reacting with an alkali metal salt of the compound of formula XI.

Compounds of formula III are new valuable intermediate products for the preparation of pharmacologically active compounds, for example the compounds of formula I.

Compounds of formula III can be obtained in a manner which is known per se, by reacting a compound of the formula II with a compound of the formula XX $$\begin{array}{c} R_2 \\ | \\ HN-Z-OH \end{array} \quad XX$$

where $R_2$ and $Z$ have the above defined meanings, in a manner which is known per se to give a compound of the formula XXI

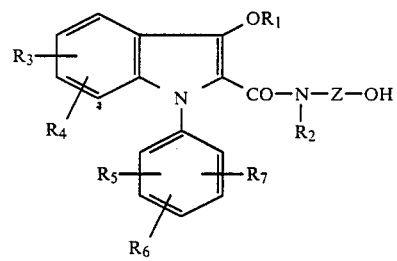

where $R_1$, $R_2$, $R_3$, $R_4$, $R_5$, $R_6$, $R_7$ and $Z$ have the above defined meanings, and then converting the hydroxyl group, in a manner which is known per se, into a group Y which can be split off by aminolysis.

The reaction of a compound of formula II with a compound of formula XX can be carried out under conditions customary for amide formation, for example under the conditions described above for the reaction of a compound of formula II with a compound of formula VI. Under such reaction conditions the desired amide formation is the predominating reaction. The terminal hydroxyl group in the compound of formula XXI can be converted into a substituent Y, which can be split off by aminolysis, in a manner which is known per se. For example, it can be reacted with a conventional halogenating agent, such as, for example, thionyl chloride, phosphorus oxychloride or phosphorus tribromide, to give a compound of formula III where Y is an appropriate halogen atom. Alternatively, the hydroxyl group can be esterified by methods which are known per se, and, for example, it can be reacted with a corresponding acid halide to give a compound of formula III where Y is a reactive ester radical, in particular one of the above-mentioned sulphonic acid radicals. In these reactions, the terminal hydroxyl groups preferentially react before any secondary hydroxyl group contained in the group Z.

Compounds of formula IVa can be obtained by reacting a compound of formula II with an amine of the formula XXII $$NH_2-R_2 \quad XXII$$

where $R_2$ has the above defined meaning, in a manner which is known per se, and the reaction can be carried out by a customary method of amide formation, for example under the conditions described above for the reaction of a compound of formula II with a compound of formula VI.

Compounds of formula IVb

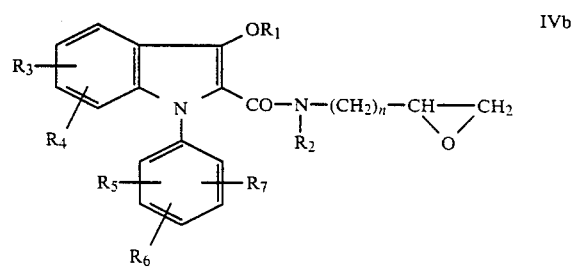

where $R_2$, $R_3$, $R_4$, $R_5$, $R_6$, $R_7$ and n have the above defined meanings, can be prepared by reacting a compound of formula IVa with a compound of formula XXIII

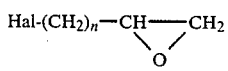

where n and Hal have the above defined meanings, in a manner which is known per se. The reaction can, for example, be carried out under the conditions described above for the reaction of a compound of formula IVa with a compound of formula VII.

If desired, some of the substituents, such as, for example, halogen, in the carbocyclic aromatic rings in the compounds of formula I or in the abovementioned intermediate products can be subsequently introduced in a manner which is known per se. Thus, the corresponding halogenated compounds can be obtained with halogenating agents, such as chlorine, bromine, N-chlorosuccinimide, N-chloroacetamide or N-bromosuccinimide.

The compounds of formula I and their pharmacologically acceptable acid addition salts exhibit interesting pharmacological properties, and have, in particular, heart-rhythmising actions. The new compounds are distinguished by a good activity and high physiological tolerance. Thus, the new compounds have a satisfactory antiarrhythmic action in low doses. Moreover, the undesirable adverse effect on the contractility of the heart is extremely low. That is to say, the relationship between the antiarrhythmic action, or the action which prolongs the refractory period of the heart, of the compounds and their negative inotropic side effects is particularly advantageous, and the compounds have a wide therapeutic range.

The antiarrhythmic action of the compounds can be demonstrated by standard pharmacological test methods.

For example, in mice, the compounds have an inhibiting effect on ventricular fibrillation caused by inhalation of chloroform. The effect of the compounds on ventricular fibrillation in mice caused by inhalation of chloroform leading to rapid cessation of breathing is determined by the method of Lawson (J. Pharmacol. Exp. Ther. 160, 22–23).

In this experimental procedure, the minimum toxic dose can also be determined at the same time. The test substance, dissolved in 0.9% strength sodium chloride solution, is administered intraperitoneally to female mice of 17–24 g body weight. The animals are kept individually in glass beakers, where they are observed for possible toxic symptoms. Ten minutes after administration of the test substance, the animals are transferred to covered 300 ml glass beakers containing a cotton-wool swab soaked with about 20 ml of chloroform. As soon as breathing begins to stop, the heart is exposed and the ventricular rhythm and rate are observed visually. The percentage of animals protected from ventricular fibrillation by the dose administered is given.

In the test described above, the compounds of formula I display antiarrhythmic actions in a dose range from 0.1 to 100 mg/kg.

The Table which follows shows the results obtained using the test method described above. The Table also shows the minimum toxic doses following intraperitoneal (i.p.) and peroral (p.o.) administration. The Example numbers given for the compounds of formula I relate to the preparation Examples below. Furthermore the compounds of formula I posses antithrombotic activities.

| Test substance of formula I Example No. | Antiarrhythmic action | | Minimum toxic dose mg/kg | |
|---|---|---|---|---|
| | Dose mg/kg ip | % of protected animals | ip | po |
| 25 | 100 | 66.7 | ≧100 | ≧300 |
| 2 | 100 | 100 | ≧100 | ≧300 |
| 15 | 100 | 100 | ≧100 | ≧300 |
| 20 | 10 | 100 | 300 | 50 |
| 1 | 25 | 100 | 300 | 100 |
| 22 | 10 | 66.7 | 300 | 50 |
| 30 | 50 | 33.3 | ≧300 | 200 |

The compounds also show an inhibiting action on disorders in cardiac rhythm induced by aconitine infusion [extrasystoles (ES), ventricular tachycardia (VT) and ventricular fibrillation (VF)] in rats in the experimental method of Raschak (Arzneimittelforsch. 25 (1975) 639–641). Thus, for example, the minimum effective doses of 2-[3-(N,N-diethylamino)-2-hydroxypropylaminocarbonyl]-3-methoxy-1-phenylindole on intravenous administration 5 minutes before the start of aconitine infusion are as follows:

| Effect | Minimum effective inhibiting dose $\mu$mol/kg |
|---|---|
| Extrasystoles | 2.15 |
| Ventricular tachycardia | 2.15 |
| Ventricular fibrillation | 4.64 |
| Heart rate | >12 |

In the test for acute toxicity, the substance has an $LD_{50}$ of 164 $\mu$mol/kg when administered intraperitoneally and of 37.3 $\mu$mol/kg when administered intravenously. This gives a therapeutic range (=quotient $LD_{50mouse}/ED_{min}$) of 8–17.

The favourable relationship between the functional refractory period prolonging action (FRP) and the contraction force reducing action (force) of the compounds can also be shown on the isolated left auricle of female guinea pigs of 300–400 g body weight by the double-stimulation method of Govier [J. Pharmakol. Exp. Ther. 148 (1965) 100–105]. The Table which follows shows the concentration in $\mu$mol/l at which the functional refractory period is increased to 125% 18 minutes after administration, and the concentration at which the contraction force is reduced to 75% of the starting value, and also the quotient of these concentrations, which is an indication of the therapeutic range of the compounds.

| Example No. | Isolated atrium from guinea pigs | | |
|---|---|---|---|
| | Force [$\mu$mol/l] | FRP [$\mu$mol/l] | Force FRP |
| 20 | 3.57 | 0.66 | 5.4 |
| 1 | 6.3 | 3.6 | 1.8 |

On the basis of the actions described above, the compounds of formula I and their pharmacologically acceptable acid addition salts are suitable as medicaments for the treatment of disorders in cardiac rhythm.

Thus, the compounds of formula I and their physiologically acceptable acid addition salts together with the customary pharmaceutical auxiliaries, carriers or excipients, can be made up into pharmaceutical preparations, such as, for example, tablets, capsules, suppositories or solutions. These preparations can be made by methods which are known per se, using the customary excipients, such as, for example, lactose, starch or talc, or liquid diluents, such as, for example, water, fatty oils or liquid paraffins.

The Examples which follow are intended to illustrate the preparation of the new compounds of formula I and of the new intermediate products in more detail, without being limiting in any way.

EXAMPLE 1

2-[3-(N,N-Diethylamino)-2-hydroxypropylaminocarbonyl]-3-methoxy-1-phenylindole (A) 475 g (5 mols) of chloroacetic acid are heated at 100° C. with 930 g (10 mols) of aniline in 2 l. of water for 1.5 hours. After the mixture has been cooled, the N-phenylglycine formed is filtered off with suction and washed with water. Yield: 468 g (=62%, relative to the chloroacetic acid).

(B) 468 g of N-phenylglycine are dissolved in 1.3 l. of methanol, with warming. A solution of 205 g of potassium hydroxide in 450 ml of methanol is added to the solution, whilst cooling. After the mixture has been cooled, the potassium salt of N-phenylglycine which has precipitated is filtered off with suction. Yield: 392 g=67%.

(C) 468 g of o-chlorobenzoic acid are dissolved in 1.5 l. of isopropanol, with warming. A solution of 198 g of potassium hydroxide in 200 ml of methanol is added to the solution, whilst cooling. After the mixture has been cooled, the potassium o-chlorobenzoate which has precipitated is filtered off with suction. Yield: 394 g=67.4%.

(D) 750 g of the potassium salt of N-phenylglycine are heated at 120° to 125° C. (internal temperature) with 808 g of potassium o-chlorobenzoate, 268 g of potassium carbonate and 1.5 g of copper powder in 385 ml of water for 5 hours. After the reaction mixture has been dissolved in water, the solution is acidified with hydrochloric acid and the N-diphenylglycine-o-carboxylic acid which has precipitated is filtered off with suction. Yield: 675 g=62.7%.

(E) 675 g of N-diphenylglycine-o-carboxylic acid, 2.5 l. of methanol and 500 ml of sulphuric acid are heated at the boiling point for 5 hours. Some of the methanol is evaporated off and the reaction mixture is then poured into water and extracted with methylene chloride. The methylene chloride phase is extracted by shaking with sodium carbonate solution, dried and evaporated, whereupon crude N-diphenylglycine-o-carboxylic acid dimethyl ester is obtained as the residue. Yield: 614 g of crude product=82.4%.

(F) 47.1 g of sodium are dissolved in 500 ml of methanol, and 500 ml of toluene are added to the solution. The mixture is heated to the boiling point, and a solution of 614 g of N-diphenylglycine-o-carboxylic acid dimethyl ester in 1.5 l. of toluene are added, under a weak reflux. After the reaction mixture has been boiled for a further 30 minutes, it is cooled, poured into 1 l. of water and acidified with 250 ml of hydrochloric acid. The N-phenylindoxylic acid methyl ester which has precipitated is filtered off with suction. Yield: 464 g=84.8%.

(G) 140 g of N-phenylindoxylic acid methyl ester, 69 ml of dimethylsulphate and 71 g of potassium carbonate in 600 ml of acetone are heated at the boiling point for 4 hours, whilst stirring. The reaction mixture is poured into water and the N-phenyl-3-methoxyindole-2-carboxylic acid methyl ester formed is filtered off with suction and dissolved in 450 ml of methanol. A solution of 42 g of sodium hydroxide in 50 ml of water is added to the solution, and the mixture is heated at the boiling point for 30 minutes. The reaction mixture is dissolved in water, the aqueous solution is acidified with hydrochloric acid and the N-phenyl-3-methoxyindole-2-carboxylic acid which has precipitated is filtered off with suction. Yield: 127 g=90.7%.

(H) 92 g of N-phenyl-3-methoxyindole-2-carboxylic acid are dissolved in 920 ml of ether and 30.3 g of pyridine. The solution is added dropwise to a solution of 28.3 ml of thionyl chloride in 160 ml of ether, whilst stirring and cooling with ice. The mixture is stirred at room temperature for 1 hour and the pyridine salts which have precipitated are filtered off with suction.

The resulting ethereal solution of N-phenyl-3-methoxyindole-2-carboxylic acid chloride is added dropwise to a solution of 579 g of 1-amino-2-hydroxy-3-diethylaminopropane and 40 g of triethylamine in 70 ml of methylene chloride, whilst cooling with ice. The reaction mixture is stirred at room temperature for 1 hour and then extracted with dilute hydrochloric acid. The hydrochloric acid extract is rendered alkaline by addition of sodium hydroxide solution and is extracted with ether. The ether solution is washed with water, dried over sodium sulphate and evaporated. 110 g of 2-[3-(N,N-diethylamino)-2-hydroxypropylaminocarbonyl]-3-methoxy-1-phenylindole remain as an oily base. This base is dissolved in isopropanol and converted into its hydrochloride. Yield: 110 g of the hydrochloride=60.6%, melting point: 148°–150° C.

EXAMPLE 2

2-[2-(N,N-Dimethylamino)-ethylaminocarbonyl]-3-hydroxy-1-(4'-chlorophenyl)-indole 16.3 g of N-(4'-chlorophenyl)-indoxylic acid methyl ester and 30 ml of 1-dimethylamino-2-aminoethane are heated at the boiling point for 2 hours. The excess amine is distilled off and the crude title compound remaining as the residue is dissolved in dilute aqueous hydrochloric acid. The hydrochloride of the title compound precipitates and is filtered off with suction. Yield: 14.1 g of crude product. The crude hydrochloride is re-precipitated three times from methanol/ether and is recrystallised once from isopropanol. Yield: 10.0 g, melting point: 188° to 189° C. (decomposition).

EXAMPLE 3

2-[3-(N,N-diethylamino)-2-hydroxypropylaminocarbonyl]-3-ethoxy-1-phenylindole.

(A) 100 g of N-phenylindoxylic acid methyl ester (prepared analogously to Example 1F) and 16.8 g of sodium hydroxide are dissolved in 400 ml of methanol. The solution is evaporated and the residue is dissolved in 300 ml of dimethylformamide. 32 ml of ethyl iodide are added in portions to this solution, and the reaction mixture is kept at 120° C. for 5 hours. The solvent is then evaporated off and the residue is extracted by stirring with cyclohexane and filtered off with suction. The solution is evaporated. 77.35 g of 3-ethoxy-1-phenylindole-2-carboxylic acid methyl ester are obtained as an oily crude product. This product can be purified by chromatography or can be employed directly in the subsequent reaction.

(B) 77.35 g of 3-ethoxy-1-phenylindole-2-carboxylic acid methyl ester, 200 ml of 50% strength ethanol and 10.5 g of sodium hydroxide are boiled under reflux for 3 hours. The solvent is then evaporated off, ice is added to the residue and the mixture is acidified with dilute hydrochloric acid. The crude 3-ethoxy-1-phenylindole-2-carboxylic acid which has precipitated is filtered off with suction. The crude product is dissolved in methylene chloride, the solution is dried with sodium sulphate and evaporated, and the residue is recrystallised from ether/petroleum ether. Yield: 25.4 g.

(C) 0.85 ml of oxalyl chloride are added to 1.42 g of 3-ethoxy-1-phenylindole-2-carboxylic acid in 10 ml of methylene chloride and the mixture is stirred at room temperature for 2 hours. It is evaporated to dryness and the residue is taken up in dioxane. The dioxane solution is evaporated again, the residue is dissolved in dioxane, and 1 ml of 3-(N,N-diethylamino)-2-hydroxypropylamine is added to the solution. When the reaction has ended, the solution is evaporated, the residue is taken up in ether, the solution is washed with saturated sodium chloride solution and the organic phase is dried and evaporated. The 2-[3-(N,N-diethylamino)-2-hydroxypropylaminocarbonyl]-3-ethoxy-1-phenylindole which remains as the residue is dissolved in isopropanol/ether, gaseous hydrogen chloride is added to the solution and the hydrochloride which crystallises out is filtered off with suction. Melting point: 146°–148° C.

EXAMPLE 4

5-Bromo-2-[3-(N,N-diethylamino)-2-hydroxypropylaminocarbonyl]-3-methoxy-1-phenylindole (A) 100 g of 3-bromo-6-chlorobenzoic acid are dissolved in 900 ml of isopropanol. 23.6 g of potassium hydroxide in 225 ml of methanol are added to the solution. The mixture is cooled, whilst stirring, and the potassium 3-bromo-6-chlorobenzoate which has precipitated out is filtered off with suction and dried. Yield: 103 g (B) 103 g of potassium 3-bromo-6-chlorobenzoate are heated at 120° C. with 68.2 g of the potassium salt of phenylglycine, 25.5 g of potassium carbonate, 0.5 g of copper powder and 90 ml of water for 4 hours. The reaction mixture is diluted with water, acidified with concentrated hydrochloric acid and extracted with methylene chloride. The organic phase is dried over sodium sulphate and filtered and the filtrate is evaporated, whereupon N-(4-bromo-2-hydroxycarbonylphenyl)-N-phenylglycine is obtained as an oily residue. Yield: 84.7 g.

(C) 84.7 g of the above acid are dissolved in 250 ml of methanol. 64 ml of sulphuric acid are added dropwise to the solution, whilst stirring, and the reaction mixture is boiled under reflux for 4 hours. The methanol is then evaporated off, the oil which remains is stirred in water and the mixture is extracted with methylene chloride. The organic phase is separated off, dried and evaporated. The dimethyl ester, of N-(4-bromo-2-hydroxycarbonylphenyl)-N-phenylglycine, which remains as an oil, is distilled in a bulb tube. Yield: 31 g of oil, boiling point$_{0.1}$: 120°–140° C.

(D) 2.1 g of sodium are dissolved in 30 ml of methanol, 30 ml of toluene are added to the solution and the mixture is heated to the boiling point. A solution of 31.1 g of the above diester in 75 ml of toluene is added dropwise, whilst the mixture is boiled under reflux. The mixture is boiled under reflux for a further hour. It is then cooled, and acidified with dilute hydrochloric acid. The 5-bromo-1-phenylindoxylic acid methyl ester which has precipitated is filtered off with suction. Yield: 12 g (E) 12 g of 5-bromo-1-phenylindoxylic acid methyl ester are suspended in 60 ml of acetone with 4.7 g of potassium carbonate. 2.5 ml of dimethyl sulphate are added to this mixture, and the mixture is boiled under reflux for 2 hours. After it has been cooled, it is diluted with water and the 5-bromo-3-methoxy-1-phenylindole-2-carboxylic acid methyl ester which has precipitated is filtered off with suction. Yield: 12.9 g (F) 12.5 g of the above ester are dissolved in 100 ml of ethanol (50% strength) and the solution is boiled under reflux with 1.6 g of sodium hydroxide for 2 hours. The ethanol is evaporated off and the aqueous solution which remains is acidified with dilute hydrochloric acid and extracted with methylene chloride. The organic phase is dried over sodium sulphate and filtered and the filtrate is evaporated. The crude 5-bromo-3-methoxy-1-phenylindole-2-carboxylic acid which remains is recrystallised from ether/petroleum ether. Melting point: 169°–173° C., yield: 7.5 g.

(G) 0.35 ml of oxalyl chloride is added to 1.75 g of the above acid in 100 ml of methylene chloride and the mixture is stirred at room temperature for 2 hours. It is then evaporated to dryness, the residue is taken up in dioxane and the mixture is again evaporated and the residue dissolved in dioxane. 1 ml of 3-(N,N-diethylamino)-2-hydroxypropylamine is added dropwise to the solution. When the reaction has ended, the mixture is evaporated, the residue is taken up in ether, the ether mixture is washed with saturated sodium carbonate solution and the organic phase is separated off, dried and evaporated. The 5-bromo-2-[3-(N,N-diethylamino)-2-hydroxypropylaminocarbonyl]-3-methoxy-1-phenylindole which remains is dissolved in isopropanol/ether, and gaseous hydrogen chloride is added to the solution, whereupon the hydrochloride of the title compound crystallises out. Melting point: 201°–203° C.

EXAMPLE 5

5-Bromo-2-[3-(N,N-diethylamino)-2-hydroxypropylaminocarbonyl]-3-methoxy-1-phenylindole 16 g of 3-methoxy-1-phenylindole-2-carboxylic acid methyl ester (prepared analogously to Example 1G) are dissolved in 250 ml of glacial acetic acid, and 1.6 ml of bromine are added dropwise to the solution. The solution is kept at 100° C. for 3 hours and is then cooled and poured onto ice. The mixture is extracted with methylene chloride, the organic phase is dried and evaporated and the 5-bromo-3-methoxy-1-phenylindole-2-carboxylic acid methyl ester which remains is crystallised from ether.

The 5-bromo-3-methoxy-1-phenylindole-2-carboxylic acid methyl ester is then further processed analogously to Example 4F and G, whereupon the hydrochloride of the title compound is obtained. Melting point: 201°–203° C.

EXAMPLE 6

5-Methyl-2[3-(N,N-diethylamino)-2-hydroxypropylaminocarbonyl]-3-methoxy-1-phenylindole (A) 12 g of 3-methoxy-5-methylindole-2-carboxylic acid methyl ester are dissolved in 25 ml of dimethylformamide. 1.5 g of sodium hydroxide (80% strength)

are added in portions to this solution. When the reaction has ended, 10 g of copper iodide are added and the reaction mixture is heated to 100° C. for half an hour. 8 ml of bromobenzene are then added and the mixture is heated at 140° C. for 20 hours, whilst stirring. After the mixture has been cooled and water and methylene chloride have been added, the inorganic substance which has precipitated is filtered off and the methylene chloride phase is separated off, dried and evaporated. The 3-methoxy-5-methyl-1-phenylindole-2-carboxylic acid methyl ester which remains, 3 g of sodium hydroxide, 3 ml of water and 30 ml of methanol are heated at the boiling point for 30 minutes. The solvent is then evaporated off, the residue is dissolved in water and the aqueous solution is extracted with ether and then acidified to pH 3 with hydrochloric acid. The 3-methoxy-5-methyl-1-phenylindole-2-carboxylic acid which has precipitated is filtered off with suction and recrystallised from cyclohexane. Melting point: 121°–122° C., yield: 9.6 g.

(B) The above 3-methoxy-5-methyl-1-phenylindole-2-carboxylic acid is converted into its acid chloride analogously to Example 1H, and this is reacted with 1-amino-3-diethylamino-2-hydroxypropane. The title compound is obtained as an oily base. This base is dissolved in isopropanol, and citric acid is added to the solution. The citrate of the title compound which has precipitated is filtered off with suction and recrystallised from isopropanol. Melting point: 126°–128° C., yield: 7.7 g.

EXAMPLE 7

2-[3-(N,N-Diethylamino)-2-hydroxypropylaminocarbonyl]-3-methoxy-1-(2',4'-dimethoxyphenyl)-indole 16.8 g of 3-methoxy-1-(2',4'-dimethoxyphenyl)-indole-2-carboxylic acid and 7 ml of triethylamine are dissolved in 50 ml of methylene chloride and the solution is added dropwise to 4 ml of thionyl chloride in 5 ml of methylene chloride. 8 g of 3-(N,N-diethylamino)-2-hydroxypropylamine dissolved in 10 ml of methylene chloride are added dropwise to this solution. The solution is poured into ice-water, the mixture is extracted with methylene chloride and the organic phase is washed with water, dried and evaporated. The 2-[3-(N,N-diethylamino)-2-hydroxypropylaminocarbonyl]-3-methoxy-1-(2', 4'-dimethoxyphenyl)-indole which remains is dissolved in isopropanol, and gaseous hydrogen chloride is added to the solution, whereupon the hydrochloride of the title compound crystallises out. Yield: 13.4 g, melting point: 166°–168° C.

EXAMPLE 8

2-[3-(N,N-Diethylamino)-2-hydroxypropylaminocarbonyl]-3-methoxy-1-phenylindole 15 g of 2-chloro-N-methyl-pyridinium iodide in 150 ml of methylene chloride and 14 ml of triethylamine are added to 13.3 g of N-phenyl-3-methoxyindole-2-carboxylic acid, dissolved in 100 ml of methylene chloride, and the mixture is stirred at room temperature for one hour. 7.5 g of 3-(N,N-diethylamino)-2-hydroxypropylamine are then added, and the mixture is stirred at room temperature for a further 3 hours. The reaction solution is added to water and the mixture is extracted with methylene chloride. The organic phase is washed with dilute sodium hydroxide solution and water, dried and evaporated. The resulting oily title compound is converted into its hydrochloride in a manner corresponding to that in Example 1. Melting point: 148°–150° C., yield: 12 g.

EXAMPLE 9

2-[3-(N,N-Diethylamino)-2-hydroxypropylaminocarbonyl]-3-methoxy-1-phenylindole 6.6 g of N-phenyl-3-methoxyindole-2-carboxylic acid and 7 ml of triethylamine in 75 ml of methylene chloride are added dropwise to 7 g of ethyl chloroformate in 25 ml of methylene chloride at −30° C. The temperature is allowed to rise slowly to 5° C., whilst stirring, and 3.7 g of 3-(N,N-diethylamino)-2-hydroxypropylamine are added. The reaction solution is subsequently stirred at room temperature, poured into water and worked up as described in Example 8. Yield: 4.5 of the hydrochloride of the title compound, melting point: 148°–150° C.

EXAMPLE 10

2-[3-(N,N-Diethylamino)-2-hydroxypropylaminocarbonyl]-3-methoxy-1-phenylindole (A) 15 g of 2-chloro-N-methyl-pyridinium iodide in 150 ml of methylene chloride and 14 ml of triethylamine are added to 13.3 g of N-phenyl-3-methoxyindole-2-carboxylic acid, dissolved in 100 ml of methylene chloride. After one hour at room temperature, 5.5 g of 3-amino-1,2-propanediol in 50 ml of pyridine are added and the reaction solution is stirred overnight. It is then evaporated, the residue is taken up in methylene chloride and the mixture is washed successively with dilute hydrochloric acid, dilute sodium hydroxide solution and saturated sodium chloride solution. After the organic phase has been dried and evaporated, the oil which remains is taken up in ethyl acetate and recrystallised. Yield: 8.1 g of 2-[2,3-dihydroxypropylaminocarbonyl]-3-methoxy-1-phenylindole.

(B) 1.7 g of 2-[2,3-dihydroxypropylaminocarbonyl]-3-methoxy-1-phenylindole and 1.2 g of p-toluenesulphonyl chloride are stirred in 20 ml of dry pyridine at room temperature for 24 hours and the reaction solution is then evaporated in vacuo, whereupon crude 2-[3-(p-toluenesulphonyloxy)-2-hydroxypropylaminocarbonyl]-3-methoxy-1-phenylindole is obtained as the residue.

(C) The crude product obtained above is taken up in 30 ml of methanol, 3 ml of diethylamine are added and the mixture is stirred at 80° C. for 24 hours. It is then evaporated, the residue is taken up in dilute hydrochloric acid and the mixture is worked up as in Example 1H to give the hydrochloride of 2-[3-(N,N-diethylamino)-2-hydroxypropylaminocarbonyl]-3-methoxy-1-phenylindole. Melting point: 148°–150° C., yield: 0.5 g.

EXAMPLE 11

2-{N-[3-(N',N'-Diethylamino)-propyl]-N-ethylaminocarbonyl}-3-methoxy-1-phenylindole 2.9 g of 2-ethylaminocarbonyl-3-methoxy-1-phenylindole (prepared from N-phenyl-3-methoxyindole-2-carboxylic acid and ethylamine analogously to Example 8) are dissolved in 35 ml of dimethylformamide, and 0.5 g of sodium hydride (80% strength) are added, whilst cooling with ice, to form the sodium salt. After 1 hour at room temperature, 1.5 g of 3-diethylaminopropyl chloride in 10 ml of dimethylformamide are added and the reaction solution is warmed to 60° C. and kept at this temperature for 2 hours. It is then evaporated in vacuo, the residue is taken up in dilute hydrochloric acid and the mixture is washed with ether. The hydrochloric acid solution is rendered alkaline with sodium carbonate solution and extracted with ether and the organic phase is dried with sodium sulphate and evaporated. The title compound is obtained as an oily base. Yield: 4.0 g.

EXAMPLE 12

2-{N-[3-(N',N'-Diethylamino)-2-hydroxypropyl]-N-ethylaminocarbonyl}-3-methoxy-1-phenylindole (A) 2.9 g of 2-ethylaminocarbonyl-3-methoxy-1-phenylindole are reacted with sodium hydride in a manner corresponding to that in Example 11. 1.0 g of epichlorohydrin in 10 ml of dimethylformamide is then added to the reaction mixture, and the reaction solution is warmed to 80° C. for 3 hours, whereupon 2-[N-(2,3-epoxypropyl)-N-ethylaminocarbonyl]-3-methoxy-1-phenylindole is formed in the reaction solution.

(B) 0.9 g of diethylamine is added to the reaction solution obtained above, and the mixture is warmed for a further 3 hours. It is then worked up in a manner corresponding to that in Example 11. 3.0 g of 2-{N-[3-(N',N'-diethylamino)-2-hydroxypropyl]-N-ethylaminocarbonyl{-3-methoxy-1-phenylindole are obtained as an oily base.

The 2-(aminoalkylaminocarbonyl)-1-phenylindole compounds of the formula I listed in the Table which follows can also be prepared from corresponding 1-phenylindole-2-carboxylic acid derivatives or -carboxylic acid amide derivatives by the processes described in Examples 1 to 12.

| Example No. | $R_1$ | $R_3$ | $R_4$ | $R_5$ | $R_6$ | $R_7$ | Z | $R_2$ | $R_8$ | $R_9$ | Salt | Melting point °C. |
|---|---|---|---|---|---|---|---|---|---|---|---|---|
| 13 | $CH_3$ | H | H | 2,3-di-$CH_3$ |  | H | $C_2H_4$ | H | $CH_3$ | $CH_3$ | HCl | 223–224 |
| 14 | $CH_3$ | H | H | 2,3-di-$CH_3$ |  | H | n-$C_3H_6$ | H | $CH_3$ | $CH_3$ | HCl | 168–170 |
| 15 | $CH_3$ | H | H | 4-Cl | H | H | $C_2H_4$ | H | $CH_3$ | $CH_3$ | HCl | 184–187 |
| 16 | $CH_3$ | H | H | 4-Cl | H | H | n-$C_3H_6$ | H | $CH_3$ | $CH_3$ | HCl | 183–187 |
| 17 | $CH_3$ | H | H | H | H | H | $C_2H_4$ | H | $CH_3$ | $CH_3$ | HCl | 202–204 |
| 18 | $CH_3$ | H | H | H | H | H | $C_2H_4$ | H | $C_2H_5$ | $C_2H_5$ | HCl | 191–192 |
| 19 | $CH_3$ | H | H | H | H | H | n-$C_3H_6$ | H | $CH_3$ | $CH_3$ | HCl | 178–180 |
| 20 | $CH_3$ | H | H | H | H | H | n-$C_3H_6$ | H | $C_2H_5$ | $C_2H_5$ | HCl | 135–137 |
| 21 | $CH_3$ | 4,5-di-Br | H | H | H | H | $CH_2-CHOH-CH_2$ | H | $C_2H_5$ | $C_2H_5$ | HCl |  |
| 22 | $CH_3$ | H | H | H | H | H | n-$C_4H_8$ | H | $C_2H_5$ | $C_2H_5$ | HCl | 115–117 |
| 23 | $C_2H_5$ | H | H | H | H | H | $C_2H_4$ | H | $CH_3$ | $CH_3$ | HCl | 179–181 |
| 24 | H | H | H | H | H | H | $C_2H_4$ | H | $CH_3$ | $CH_3$ | HCl | 188–193 |
| 25 | H | H | H | 2,3-di-$CH_3$ |  | H | $C_2H_4$ | H | $CH_3$ | $CH_3$ | HCl | 212–213 |
| 26 | $CH_3$ | H | H | H | H | H | $CH_2CHOH-CH_2$ | H | -n-$C_4H_8-$ |  | HBr | 164–165 |
| 27 | $CH_3$ | H | H | H | H | H | $CH_2-CHOH-CH_2$ | H | -n$C_5H_{10}-$ |  | HBr | 206–207 |
| 28 | $CH_3$ | H | H | H | H | H | $CH_2-CHOH-CH_2$ | H | $-C_2H_4OC_2H_4-$ |  | HCl | 195–196 |
| 29 | $CH_3$ | H | H | H | H | H | $CH_2-CHOH-CH_2$ | H | $-C_2H_4SC_2H_4-$ |  | HBr | 217–218 |
| 30 | $CH_3$ | 5-Br | H | H | H | H | $C_2H_4$ | H | $CH_3$ | $CH_3$ | HCl | 238–242 |
| 31 | $CH_3$ | 5-Br | H | H | H | H | n-$C_3H_6$ | H | $C_2H_5$ | $C_2H_5$ | HCl | 177–179 |
| 32 | $CH_3$ | 4,5-di-Br | H | H | H | H | n-$C_3H_6$ | H | $C_2H_5$ | $C_2H_5$ | HCl | 222–226 |
| 33 | $CH_3$ | 4,5-di-Br | H | H | H | H | $C_2H_4$ | H | $CH_3$ | $CH_3$ | HCl |  |
| 34 | $C_2H_5$ | H | H | H | H | H | n-$C_3H_6$ | H | $C_2H_5$ | $C_2H_5$ | HCl | 154–256 |
| 35 | n-$C_7H_{15}$ | H | H | H | H | H | $CH_2-CHOH-CH_2$ | H | $C_2H_5$ | $C_2H_5$ | Base | oil |
| 36 | n-$C_3H_7$ | H | H | H | H | H | $CH_2-CHOH-CH_2$ | H | $C_2H_5$ | $C_2H_5$ | HCl | 120–123 |
| 37 | $C(CH_3)_3$ | H | H | H | H | H | $CH_2CHOH-CH_2$ | H | $C_2H_5$ | $C_2H_5$ |  |  |
| 38 | $CH_2-CH(CH_3)_2$ | H | H | H | H | H | $CH_2-CHOH-CH_2$ | H | $C_2H_5$ | $C_2H_5$ |  |  |
| 39 | $CH_3$ | H | H | 4-$OCH_3$ | H | H | $CH_2-CHOH-CH_2$ | H | $C_2H_5$ | $C_2H_5$ | HCl | 204–205 |
| 40 | $CH_3$ | H | H | 3-Br | H | H | $CH_2-CHOH-CH_2$ | H | $C_2H_5$ | $C_2H_5$ | HCl | 135–137 |
| 41 | $CH_3$ | 7-$CH_3$ | H | H | H | H | $CH_2-CHOH-CH_2$ | H | $C_2H_5$ | $C_2H_5$ | HCl | 125–127 |
| 42 | $CH_3$ | H | H | 2-$CH_3$ | 3-Cl | H | $CH_2-CHOH-CH_2$ | H | $C_2H_5$ | $C_2H_5$ | HCl | 219–221 |
| 43 | $CH_3$ | 5,6-di-$OCH_3$ | H | H | H | H | $CH_2-CHOH-CH_2$ | H | $C_2H_5$ | $C_2H_5$ | Base | oil |
| 44 | $CH_3$ | 4-Cl | H | H | H | H | $CH_2-CHOH-CH_2$ | H | $C_2H_5$ | $C_2H_5$ | HCl | 141–143 |
| 45 | $CH_3$ | 5-Cl | H | H | H | H | $CH_2-CHOH-CH_2$ | H | $C_2H_5$ | $C_2H_5$ | Cit. | 113–115 |
| 46 | $CH_3$ | 6-Cl | H | H | H | H | $CH_2-CHOH-CH_2$ | H | $C_2H_5$ | $C_2H_5$ | Cit. | 125–126 |
| 47 | H | H | H | H | H | H | $CH_2-CHOH-CH_2$ | H | $C_2H_5$ | $C_2H_5$ | HCl | 166–168 |
| 48 | cyclohexyl | H | H | H | H | H | $CH_2-CHOH-CH_2$ | H | $C_2H_5$ | $C_2H_5$ |  |  |
| 49 | $CH_2$-cyclohexyl | H | H | H | H | H | $CH_2-CHOH-CH_2$ | H | $C_2H_5$ | $C_2H_5$ |  |  |
| 50 | $CH_2-CH=CH_2$ | H | H | H | H | H | $CH_2-CHOH-CH_2$ | H | $C_2H_5$ | $C_2H_5$ |  |  |
| 51 | $CH_2$-cyclopropyl | H | H | H | H | H | $CH_2-CHOH-CH_2$ | H | $C_2H_5$ | $C_2H_5$ |  |  |

HCl = Hydrochloride,
HBr = Hydrobromide,
Cit = Citrate,
Base = free base

EXAMPLE I: TABLETS

Tablets having the following composition per tablet are prepared:

| | |
|---|---|
| 2-[3-(N,N-diethylamino)-2-hydroxypropyl-aminocarbonyl]-3-methoxy-1-phenyl-indole hydrochloride | 25 mg |
| corn starch | 60 mg |
| Lactose | 130 mg |
| Gelatin (as a 10% strength solution) | 6 mg |

The active compound, the maize starch and the lactose are made into a paste with the 10% strength gelatin solution. The paste is comminuted and the resulting granules are placed on a suitable metal sheet and dried at 45° C. The dried granules are passed through a comminuting machine and mixed with the further auxiliaries below in a mixer:

| | |
|---|---|
| Talc | 5 mg |
| Magnesium stearate | 5 mg |
| corn starch | 9 mg | and the mixture is then pressed to tablets weighing 240 mg.

EXAMPLE II: SUPPOSITORIES

Suppositories having the following composition per suppository are prepared:

| | |
|---|---|
| 2-[3-(N,N-diethylamino)-2-hydroxypropyl-aminocarbonyl]-3-methoxy-1-phenyl-indole hydrochloride | 25 mg |
| Cacao butter | 1,975 mg |

The active compound and the finely ground suppository mass are mixed thoroughly and the mixture is then melted. Suppositories weighing 2 g are cast from the melt, which is kept homogeneous by stirring.

EXAMPLE III

Injection Solution

An injection solution having the following composition per ml is prepared:

| | |
|---|---|
| 2-[3-(N,N-diethylamino)-2-hydroxypropyl-aminocarbonyl]-3-methoxy-1-phenyl-indole hydrochloride | 25 mg |
| Dimethylacetamide | 100 mg |
| Propylene glycol | 500 mg |
| Benzyl alcohol | 15 mg |
| Ethanol | 100 mg |
| Water for injection purposes to 1 ml. | |

The active compound is dissolved in the dimethylacetamide, and the benzyl alcohol, propylene glycol, ethanol and water are added. The mixture is filtered through a candle filter and filled into suitable ampoules and the ampoules are sealed and sterilised.

We claim:

1. A compound of the general formula IId

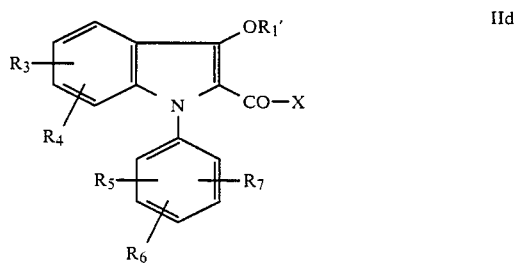

wherein $R_1'$ is an alkyl, alkenyl, cycloalkyl or cycloalkylalkyl radical with up to 7 carbon atoms, $R_3$ is a hydrogen or halogen atom, or a lower alkyl, hydroxyl or lower alkoxy radical, $R_4$ is a hydrogen or halogen atom, or a lower alkyl, hydroxyl or lower alkoxy radical, or, if $R_3$ is a hydrogen atom, $R_4$ may be a nitro or trifluoromethyl radical, or $R_3$ and $R_4$ are bonded to adjacent carbon atoms and together denote a methylenedioxy or an ethylenedioxy radical, $R_5$ is a hydrogen or halogen atom, or a lower alkyl, hydroxyl or lower alkoxy radical and $R_6$ is a hydrogen or halogen atom, or a lower alkyl, lower alkoxy or hydroxyl radical or, if $R_5$ is a hydrogen atom, $R_6$ may be a nitro or trifluoromethyl radical, or $R_5$ and $R_6$ are bonded to adjacent carbon atoms and together denote a methylenedioxy or ethylenedioxy radical, $R_7$ is a hydrogen atom, or, if $R_5$ and $R_6$ are lower alkoxy radicals, $R_7$ may also be a lower alkoxy radical and X is a hydroxyl group.

2. A compound as claimed in claim 1, wherein $R_1'$, $R_3$, $R_4$, $R_5$, $R_6$ and $R_7$ have the meanings defined in claim 1 and X is a halogen atom, or a hydroxyl, lower alkoxy or O-CO-W radical, where W is a lower alkyl or lower alkoxy radical.

* * * * *